United States Patent
Fujimoto et al.

[11] Patent Number: 5,866,084
[45] Date of Patent: Feb. 2, 1999

[54] WEB STERILIZING DEVICE

[75] Inventors: Akimasa Fujimoto; Hidekimi Yamamoto; Michio Ueda, all of Tokushima, Japan

[73] Assignee: Shikoku Kakoki Co., Ltd., Tokushima, Japan

[21] Appl. No.: 944,441

[22] Filed: Oct. 6, 1997

[30] Foreign Application Priority Data

Oct. 7, 1996 [JP] Japan .................................. 8-266423

[51] Int. Cl.⁶ ..................................................... A61L 2/18
[52] U.S. Cl. ............................ 422/300; 422/28; 422/304
[58] Field of Search ............................. 422/28, 292, 300, 422/302, 303, 304

[56] References Cited

U.S. PATENT DOCUMENTS 3,634,099  1/1972  Wilson ...................................... 422/38
5,077,010  12/1991  Ishizaka et al. ......................... 422/102
5,199,346  4/1993  Hadley et al. ........................... 422/304

*Primary Examiner*—Krisanne Thornton
*Assistant Examiner*—Fariborz Moazzam
*Attorney, Agent, or Firm*—Armstrong, Westerman, Hattori, McLeland, and Naughton

[57] ABSTRACT

A web sterilizing device comprising a sterilizing solution tank 51, web guide means for guiding a web W so as to bring the web w into the tank 51, dip the web w in a sterilizing solution within the tank 51 and thereafter move the web W out of the tank 51, a pair of endless chains 105 extending in parallel to each other both inside and outside the tank 51, chain guide means for guiding the chains 105 so as to move the chains 105 along respective opposite sides of a path for the web W to move along by being guided through the tank 51 by the web guide means, and a web engaging member 133 extending between and connected to the chains 105.

3 Claims, 2 Drawing Sheets

WEB STERILIZING DEVICE

BACKGROUND OF THE INVENTION

The present invention relates to a web sterilizing device for use in packaging machines for producing closed content-filled rectangular parallelepipedal containers from a web of packaging material.

As disclosed, for example, in JP-A No. 60-110628, devices of the type mentioned are already known which comprise a sterilizing solution tank, web guide means for guiding a web so as to bring the web into the tank, dip the web in a sterilizing solution within the tank and thereafter move the web out of the tank, an endless chain extending both inside and outside the tank, chain guide means for guiding the chain so as to move the chain along one side of a path for the web to move along by being guided through the tank by the web guide means, and a web engaging pin attached to the chain.

One edge portion of the web is caught by the engaging pin on the chain, with the other edge portion left free. When moved to pull the web, the chain fails to smoothly pull the web if the leading end edge portion of the web loosens.

SUMMARY OF THE INVENTION

An object of the present invention is to provide a web sterilizing device wherein the web can be pulled smoothly without the likelihood of the web loosening.

The present invention provides a web sterilizing device comprising a sterilizing solution tank, web guide means for guiding a web so as to bring the web into the tank, dip the web in a sterilizing solution within the tank and thereafter move the web out of the tank, a pair of endless chains extending in parallel to each other both inside and outside the tank, chain guide means for guiding the chains so as to move the chains along respective opposite sides of a path for the web to move along by being guided through the tank by the web guide means, and a web engaging member extending between and connected to the chains.

With the web sterilizing device embodying the invention, the leading end portion of the web can be engaged over the entire width of the web by the engaging member, so that the web can be pulled over the entire width. The web can therefore be pulled smoothly without the likelihood of the web loosening.

Preferably, the web engaging member is formed with a slit for inserting the leading end portion of the web therethrough.

The web leading end portion can be engaged with the engaging member by inserting the leading end portion over a relatively great length through the slit and folding over the end portion.

Preferably, the web sterilizing device has outside the tank sprockets having the respective chains reeved therearound and a manual handle attached to a drive shaft fixedly provided with the sprockets.

The chains can be driven readily by the handle.

DESCRIPTION OF THE PREFERRED EMBODIMENT

An embodiment of the invention will be described below with reference to the drawings.

In the following description, the terms "left" and "right" are used based on FIG. 1 and refer respectively to the left-hand side and the right-hand side of FIG. 1. The terms "front" and "rear" are used with respect to a direction orthogonal to the plane of FIG. 1 and refer to the front side and the rear side thereof, respectively.

Figure 1:
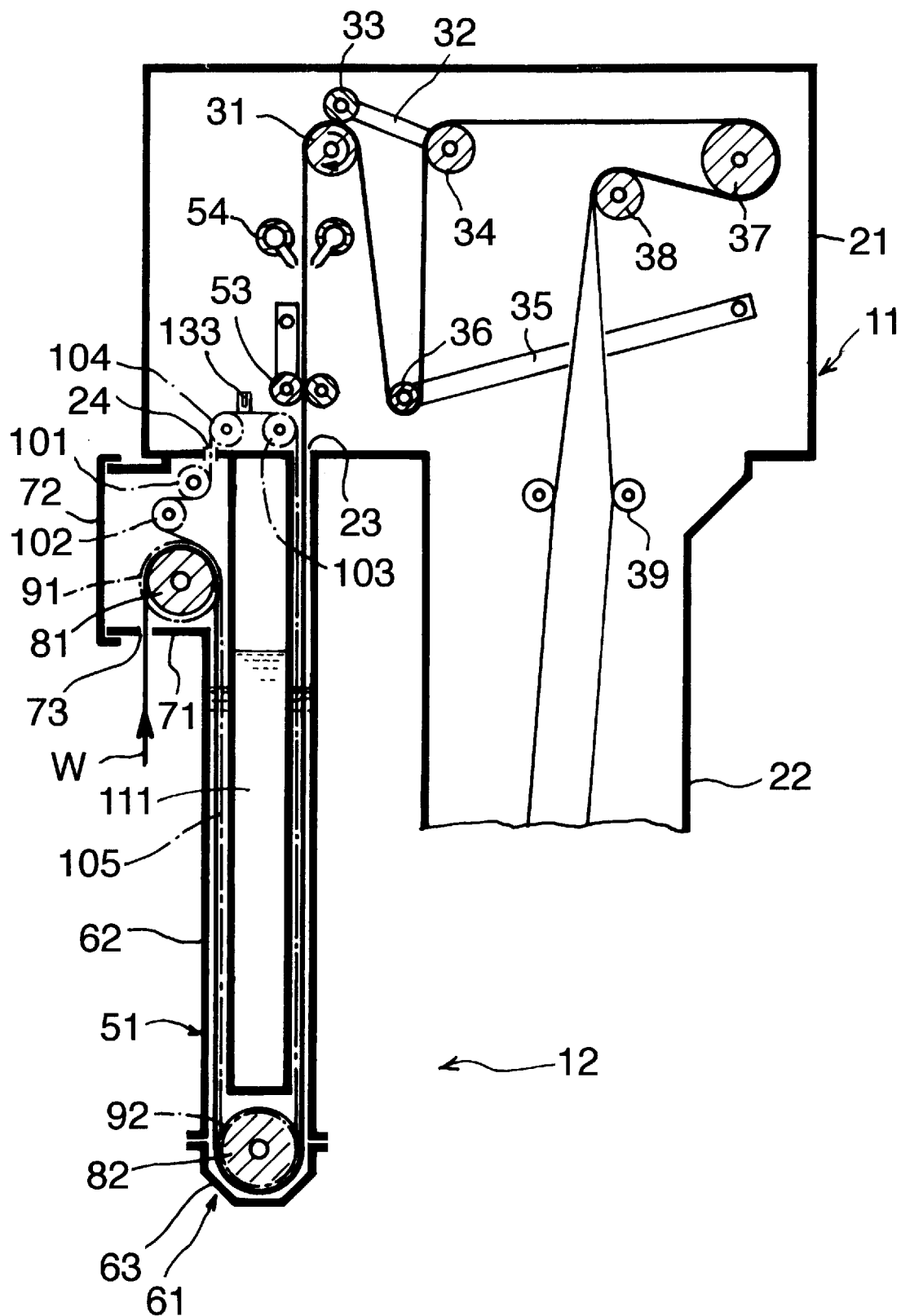
FIG. 1 is a view in vertical section of a web sterilizing device embodying the invention.

FIG. 1 shows an aseptic chamber 11 providing a packaging work space for shaping a web W into a tubular form and filling contents into the tube, and a web sterilizing device 12 for sterilizing the web W to be guided into the aseptic chamber 11.

The aseptic chamber 11 comprises an upper compartment 21 in the form of a horizontally elongated box, and a lower compartment 22 in the form of a vertically elongated box and extending downward from the approximate right half of the compartment 22. The upper compartment 21 has a bottom wall which is formed with a web inlet 23 and chain holes 24 at the left thereof.

A feed roller 31 is disposed inside the upper compartment 21 above the web inlet 23. A left arm 32 pivotally movable upward and downward has a free end positioned close to the top of the feed roller 31 and carrying a holding roller 33, which is pressed against the roller 31 from above. Arranged at the right of the feed roller 31 are a left small bending roller 34 and a right large bending roller 37. A right arm 35 pivotally movable upward and downward has a free end carrying a dancer roller 36, which is positioned below the space between the feed roller 31 and the small bending roller 34. A zigzag travel correcting roller 38 is disposed between the two bending rollers 34, 37 slightly therebelow. A forming roller ring 39 is positioned below the correcting roller 38.

The web W is upwardly led into the upper compartment 21 through the inlet 23, passed between the feed roller 31 and the holding roller 33 first, then reeved around the dancer roller 36, small bending roller 34, large bending roller 37 and correcting roller 38 successively, guided downward from the roller 38, inserted through the forming roller ring 39 and sent into the lower compartment 22. Inside the compartment 22, the web W is formed into a tube, which is then filled with contents. The content-filled tube is led out from the aseptic chamber 11, transversely sealed and cut at an interval corresponding to the length of one container, and thereby made into pillowlike unfinished containers. The unfinished containers are eventually shaped into a rectangular parallelepidal form, whereby completed containers are obtained.

The web sterilizing device 12 comprises a sterilizing solution tank 51 containing an aqueous solution of hydrogen peroxide having a concentration of 30 to 35%, and a pair of squeeze rollers 53 and a pair of air knives 54 arranged at opposite sides of the path of travel of the web from the web inlet 23 to the feed roller 31.

The sterilizing solution tank 51 comprises a tank body 62 in the form of a tube having a rectangular cross section and a width in the left-right direction and opened at its upper and lower ends, the lower-end opening serving as an inspection opening 61, and a bottom closure 63 for closing the opening 61.

The tank body 62 has its upper-end opening covered with the bottom wall of the upper compartment 21. A work compartment 71 extends leftward from the left side of upper end portion of the tank body 62 and is in communication with the interior of the body. The work compartment 71 is open at its left side, with a door 72 provided for the opening, and has a bottom wall formed with a web inlet 73.

An upper web guide roller 81 is disposed inside the work compartment 71. A lower web guide roller 82 is disposed in the bottom portion of the solution tank 51.

The web W is upwardly placed into the work compartment 71 through the inlet 73, reeved around the upper web guide roller 81, led into the tank 51 downward, turned around the lower web guide roller 82 upward through the tank 51 and guided to the web inlet 23 of the aseptic chamber 11.

A pair of front and rear large sprockets 91 are arranged respectively at the front and rear sides of the upper web guide roller 81 concentrically with the roller 81 but rotatably independently thereof. Similarly, a pair of front and rear large sprockets 92 are arranged respectively at the front and rear sides of the lower web guide roller 82 concentrically with the roller 82 but rotatably independently thereof. Arranged above the respective upper large sprockets 91 within the work compartment 71 are a pair of first small sprockets 101 and a pair of second small sprockets 102. Further arranged in the upper compartment 21 are a pair of third small sprockets 103 at the left of the web inlet 23 immediately adjacent thereto, and a pair of fourth small sprockets 104 at the right of the respective chain holes 24 immediately adjacent thereto. The spacing between each of the pairs of first to fourth small sprockets 101 to 104 is equal to the spacing between the large sprockets 91, 92. A pair of front and rear endless chains 105 are reeved around the upper and lower large sprockets 91, 92 and the first to fourth small sprockets 101 to 104, respectively at the front and rear sides. In the interior of the solution tank 51, the paths of movement of the chains 105 extend respectively along the front and rear edges of the path of travel of the web.

A hot water tank 111 is provided within the solution chamber 51 between the paths of downward movement of the web W and chains 105 and the paths of upward movement thereof. The hot water tank 111 has an upper end covered with the bottom wall of the upper compartment 21, and front and rear ends with the front and rear walls of the tank 51.

Figure 2:
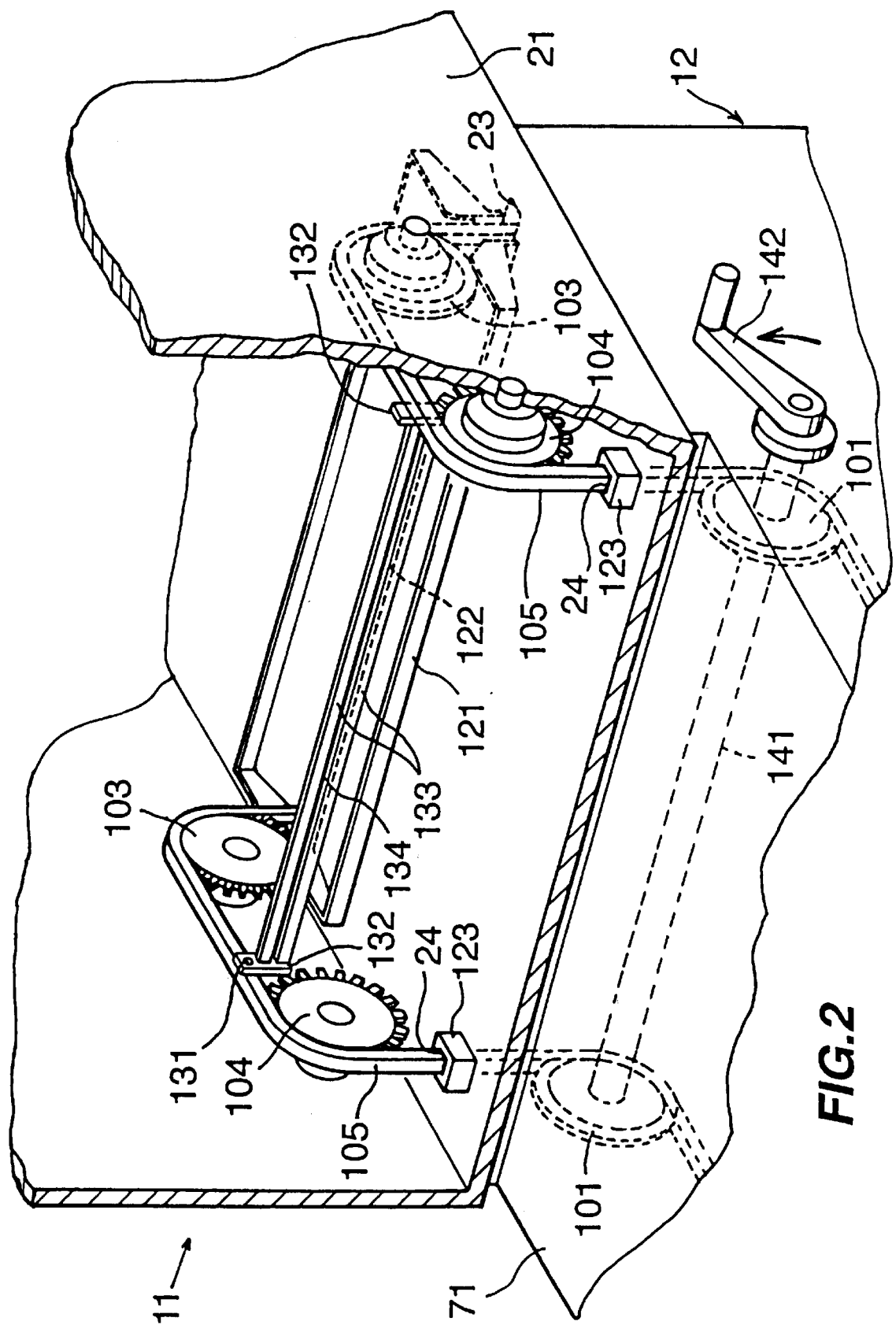
FIG. 2 is a fragmentary perspective view of the device.

With reference to FIG. 2, a shallow troughlike receptacle 121 for receiving the sterilizing solution is provided around the web inlet 23 of the aseptic chamber 11 and formed in its bottom wall with a slit 122 communicating with the web inlet 23. A seal member 123 is provided between the edge portion defining each chain hole 24 and the chain 105.

A pair of mount pins 131 are attached to the respective front and rear chains 105, as inwardly directed toward each other. A pair of rotatable pieces 132 are attached to the respective mount pins 131. Web engaging bars 133 extend between and are eccentrically attached to the rotatable pieces 132. A slit 134 is formed between the bars 133 nearly over the entire length thereof.

FIG. 2 shows the web engaging bars 133 as positioned at the right of the fourth small sprockets 104 immediately adjacent thereto. The bars 133 are allowed to stand by in this position during the steady-state packaging operation.

The front and rear first small sprockets 101 are fixed to a horizontal drive shaft 141, which has a front end portion extending through the front wall of the work compartment 71 to project forward. A manual handle 142 is fastened to the forward projecting end of the drive shaft 141.

Before the start of packaging operation, the web W is passed through the sterilizing solution tank 51 by the following procedure.

With the door 72 opened, the leading end of the web W is passed through the inlet 73 of the work compartment 71, and a 2- to 3-meter-long portion of the web W from its leading end is hauled into the compartment 71. When the handle 142 is turned counterclockwise as indicated by an arrow in FIG. 2, the chains 105 are moved clockwise. The web engaging bars 133 also move with the movement of the chains 105. The chains 105 are halted when the web engaging bars 133 are brought to a position between the upper large sprockets 81 and the second small sprockets 102.

The leading end of the web W is inserted through the slit 134 between the bars 133 and wound around the bars in this state. The handle 142 is then turned clockwise in FIG. 2, whereby the chains 105 are moved counterclockwise in FIG. 2 while pulling the web W. The web W moved by being pulled by the chains 105 passes over the upper guide roller 81, descends from the work compartment 71 to dip into the sterilizing solution, reaches the bottom of the tank 51, thereafter turns around the lower guide roller 82 to move upward, and is passed through the inlet 23 of the aseptic chamber 11. When the web W has been thus passed through the solution tank 51, the leading end of the web W is released from the engaging bars 133 and thereafter guided to a suitable location by pulling the web W by hand.

What is claimed is:

1. A web sterilizing device, comprising:

a sterilizing solution tank;

web guiding means for guiding a web so as to bring the web into the tank, dip the web in a sterilizing solution within the tank and thereafter move the web out of the tank;

a pair of endless chains extending in parallel to each other both inside and outside the tank;

chain guiding means for guiding the chains so as to move the chains along respective opposite sides of a path for the web to move along by being guided through the tank by the web guide means;

and a single web engaging member extending in a transverse direction of said endless chains and connected thereto, wherein said web engaging member extends completely across said pair of endless chains.

2. A web sterilizing device as defined in claim 1 wherein the web engaging member is formed with a slit for inserting a leading end of the web therethrough.

3. A web sterilizing device as defined in claim 1 or 2 which has outside the tank sprockets having the respective chains reeved therearound and a manual handle attached to a drive shaft fixedly provided with the sprockets.

\* \* \* \* \*